(12) United States Patent
Rauscher et al.

(10) Patent No.: US 6,899,736 B1
(45) Date of Patent: May 31, 2005

(54) SHOULDER JOINT PROSTHESIS

(75) Inventors: Markus Rauscher, Allenwinden (CH); Peter Wendt, Wiesendangen (CH)

(73) Assignee: Centerpulse Orthopedics, Ltd., Baar (CH)

( * ) Notice: Subject to any disclaimer, the term of this patent is extended or adjusted under 35 U.S.C. 154(b) by 0 days.

(21) Appl. No.: 10/646,064

(22) Filed: Aug. 21, 2003

(30) Foreign Application Priority Data

Aug. 21, 2002 (EP) .................................. 02018730
May 7, 2003 (EP) .................................. 03010285

(51) Int. Cl.[7] .............................................. A61F 2/40
(52) U.S. Cl. ................................................ 623/19.12
(58) Field of Search ..................... 623/19.11, 19.12, 623/19.13, 19.14, 22.12, 23.11, 23.12, 23.13

(56) References Cited

U.S. PATENT DOCUMENTS

| 4,003,095 | A | | 1/1977 | Gristina |
| 5,358,526 | A | * | 10/1994 | Tornier ..................... 623/19.14 |
| 5,569,263 | A | | 10/1996 | Hein |
| 5,741,335 | A | | 4/1998 | Gerber et al. |
| 5,885,295 | A | | 3/1999 | McDaniel et al. |
| 6,045,582 | A | * | 4/2000 | Prybyla ..................... 623/19.11 |
| 6,197,063 | B1 | | 3/2001 | Dews |
| 6,203,575 | B1 | | 3/2001 | Farey |
| 6,406,496 | B1 | | 6/2002 | Ruter |
| 2004/0034431 | A1 | * | 2/2004 | Maroney et al. ......... 623/19.14 |

FOREIGN PATENT DOCUMENTS

| EP | 0 679 375 A1 | 11/1995 |
| EP | 0 931 522 A1 | 7/1999 |
| EP | 0 953 321 A1 | 11/1999 |
| EP | 1 314 407 A1 | 5/2003 |
| EP | 1 321 114 A1 | 6/2003 |
| WO | WO 97/25943 A1 | 7/1997 |
| WO | WO 99/37254 A1 | 7/1999 |

* cited by examiner

*Primary Examiner*—Bruce E Snow
(74) *Attorney, Agent, or Firm*—Christie, Parker & Hale, LLP

(57) ABSTRACT

The invention relates to a shoulder joint prosthesis comprising two cooperating bearing bodies, a shaft and a coupling for the connection of the shaft to one of the bearing bodies, with a support member adjoining the lower side of the bearing member connectable to the shaft, an outer support surface of said support member at least partly filling a gap present between the bearing body and the shaft in the state connected to the shaft such that the growing together of bone fragments is promoted.

14 Claims, 10 Drawing Sheets

Figure 8:
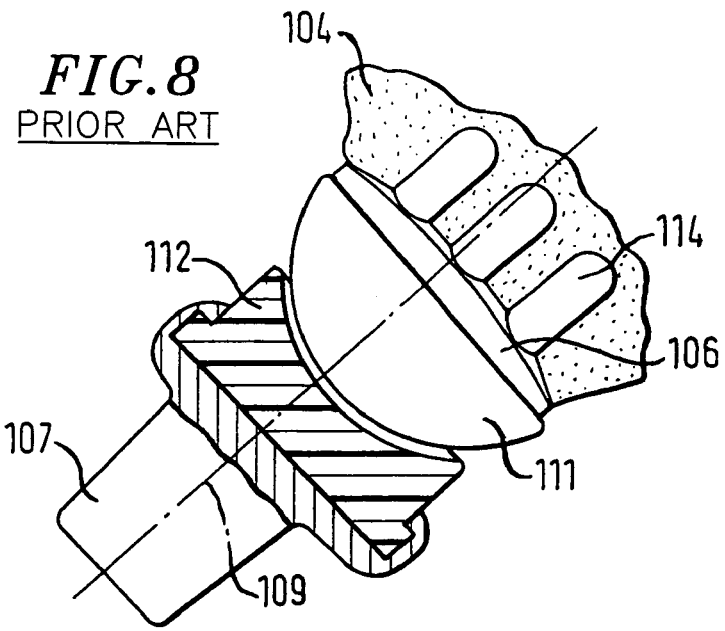

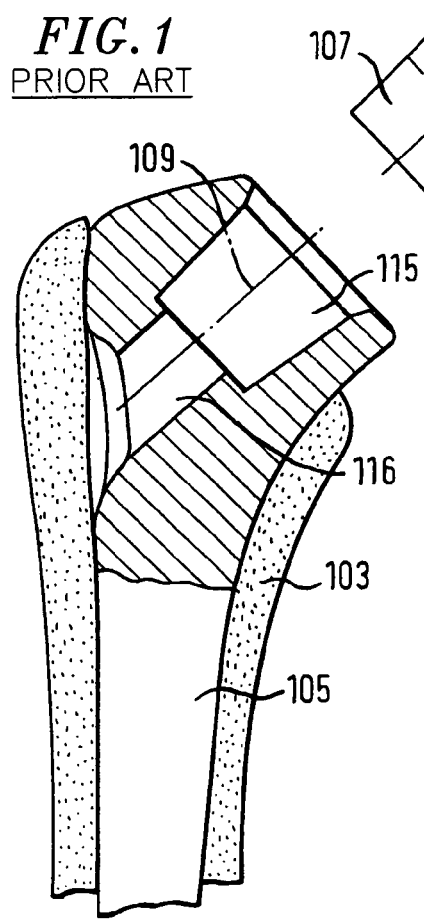
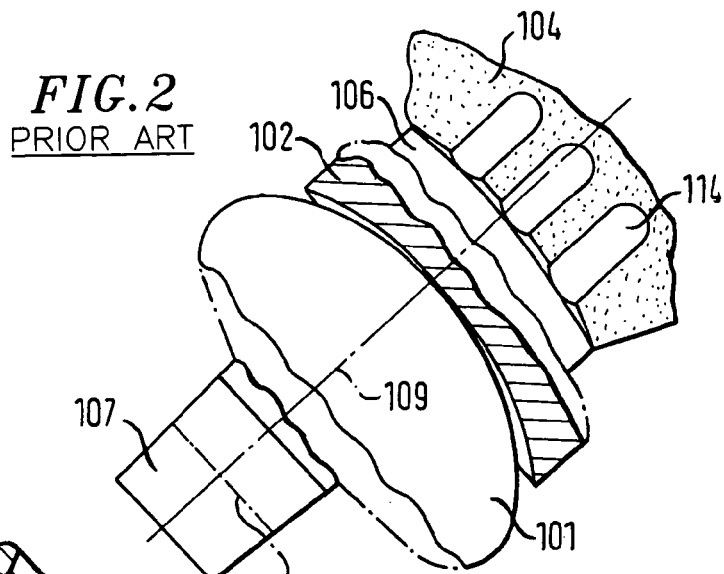
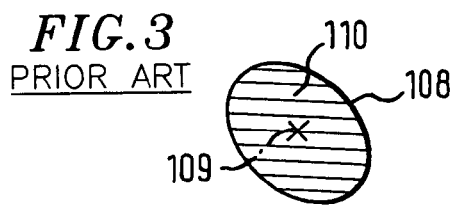
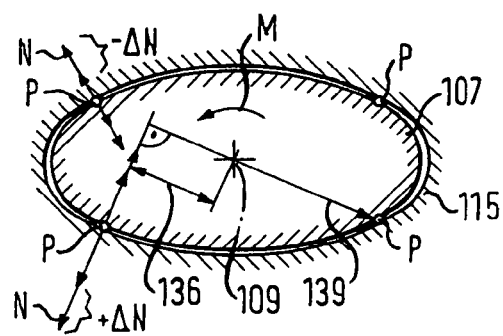
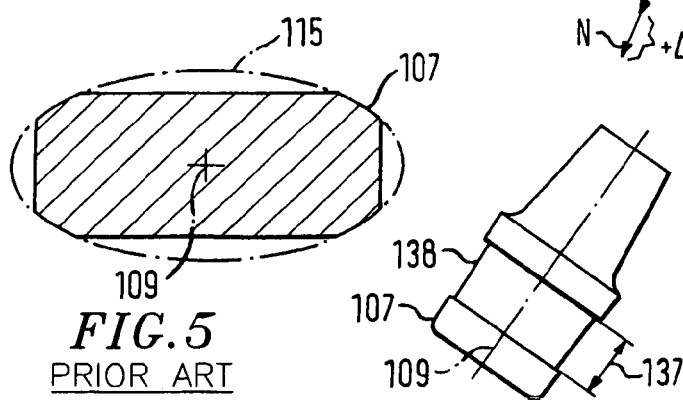

SHOULDER JOINT PROSTHESIS

CROSS REFERENCE TO RELATED APPLICATION

This application claims priority of European Patent Application No. 02 018 730.8 filed on Aug. 21, 2002, and European Application No. 03 010 285.9 filed on May 7, 2003.

The invention relates to a shoulder joint prosthesis comprising two cooperating bearing bodies, a shaft and a coupling to couple the shaft to one of the bearing bodies.

Such a prosthesis is known, for example, from the European patent applications EP 01 811 120.3 and EP 02 018 730.8.

In such a flexible system, the shaft to be inserted into the upper arm is not fixedly connected to the bearing body, but bearing bodies suitable for the respective case and selectable from a modular system can be connected to the shaft via the coupling, with it moreover being possible to realize different positions of the bearing body relative to the shaft. This flexibility makes it necessary to design the shaft such that sufficient space is present in the region of the transition between the shaft and the bearing body to attach different bearing bodies or to make different relative positions of the bearing bodies possible. In cases of fractures with a plurality of small bone fragments, problems can occur in the growing together of the individual fragments.

It is the object of the invention to provide optimum results even with fractures comprising a plurality of small bone fragments with a shoulder joint prosthesis of the initially named kind while maintaining flexibility and without impairment of the connection between the bearing body and the shaft.

This object is satisfied by the features of claim 1 and in particular in that a support member adjoins the lower side of the bearing body which can be connected to the shaft, an outer support surface of said support member at least partly filling a gap present between the bearing body and the shaft in the state connected to the shaft such that the growing together of bone fragments is promoted.

In accordance with the invention, the intermediate space between the shaft and the bearing body is bridged by the support member, whereby a substructure is advantageously created at which bone fragments can support themselves, which promotes their growing together.

The invention is generally independent of whether the bearing body is a bearing head or a bearing shell.

In a further development of the invention, the support surface of the support member is made convex at least regionally.

Provision can furthermore be made for the jacket surface of the shaft and the support surface of the support member to together form an area which is at least substantially closed and adjoins the lower side of the bearing body.

The support surface of the support member can adjoin the jacket surface of the shaft at least approximately tangentially.

The growing on of bone material is further promoted when, in accordance with an embodiment of the invention, the support surface of the support member is structured.

The support surface of the support member is in particular made free of apertures.

The support member can be replaceably connected to the bearing body. A modular construction can hereby advantageously be realized in which a plurality of bearing bodies can be combined with a plurality of protective bodies to form an ideally suitable configuration for the respective application.

Provision can furthermore be made in accordance with the invention for at least one recess to be present between the shaft and the support member, when the bearing body is connected to the shaft, at which a tool can be positioned to release the bearing body from the shaft.

The shaft can be provided with a support element which is laterally mounted at the shaft and whose outer side forms the jacket surface of the shaft merging into the support surface of the support member in the region of the transition from the shaft into the support member. The support element can in particular be made in a basket or shell like shape.

The support element can furthermore be fixedly connected, for example welded, to the shaft. Alternatively, the support element can be made in one piece with the shaft.

In a further embodiment of the invention, the support element can be provided with apertures.

Provision can furthermore be made for the proportion of the sections of the outer surface of the support element which is broken up due to the apertures to lie in the range from 35% to 45% along a peripheral line of the support element which lies in a plane extending perpendicular to the shaft axis and at a spacing of 8 mm from the intersecting point between the shaft axis and the head axis or shell axis in the proximal direction in the implanted state.

Provision can furthermore be made for the X/Y ratio of the maximum outer diameter of the support element in the sagittal direction X and the of the maximum outer diameter of the support element in the transverse direction Y to lie in the range from 0.85 to 0.95 with respect to the orientation of the support element in the implanted state with a shaft axis extending perpendicular to the transverse plane.

For the connection to the shaft, the coupling can include a clamping section with which a firm clamping seat of the coupling in the shaft can be established by introduction, in particular by hammering, into a coupling reception of the shaft, in particular a clamping seat which is releasable again.

Provision can be made for the clamping section to taper like a cone and to be able to be introduced into a correspondingly shaped counter shape of the shaft serving as a coupling reception.

Provision can furthermore be made for the clamping section to form a shape matched connection with the counter shape in its state connected to the shaft which is rotationally fixed with respect to a longitudinal axis and is wedged due to its conical shape. A self-locking seat of the clamping section in the counter shape can hereby be realized.

The clamping section can have a cross-section deviating from a circular shape. The cross-section of the clamping section is preferably elliptical.

Provision can be made for the elliptical cross-section of the clamping section and of the counter shape of the shaft to be aligned in its plane such that the major axis of the ellipse appears as a perpendicular in projection toward lateral.

It has been found that an optimum utilization of the material and a maximum strength for the clamping connection between the clamping section and the counter form can hereby be achieved.

Provision can furthermore be made for the shaft to have, in the plane of the elliptical cross-section, the outline of a rectangle provided with rounded corners whose long sides extend parallel to the major axis of the ellipse.

Further embodiments of the invention are recited in the dependent claims, in the description and in the drawing.

The invention will be described in the following by way of example with reference to the drawing. There are shown:

FIG. 1 schematically, a shaft of a shoulder joint prosthesis of the prior art implanted in a humerus;

FIG. 2 schematically, an artificial shoulder joint comprising a bearing body which is formed as a bearing head in accordance with the prior art and which has a conical body to match the shaft of FIG. 1;

FIG. 3 schematically, a cross-section through a conical body in accordance with FIG. 2 with an elliptically extending periphery.

Figure 7:
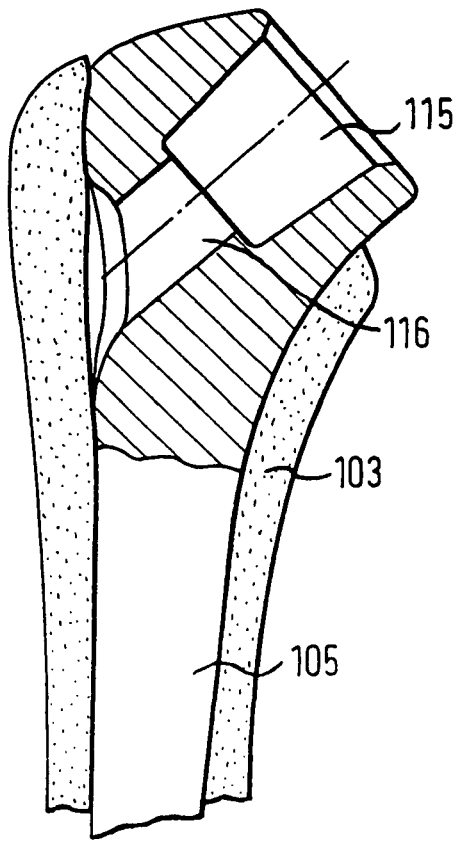
Figure 9:
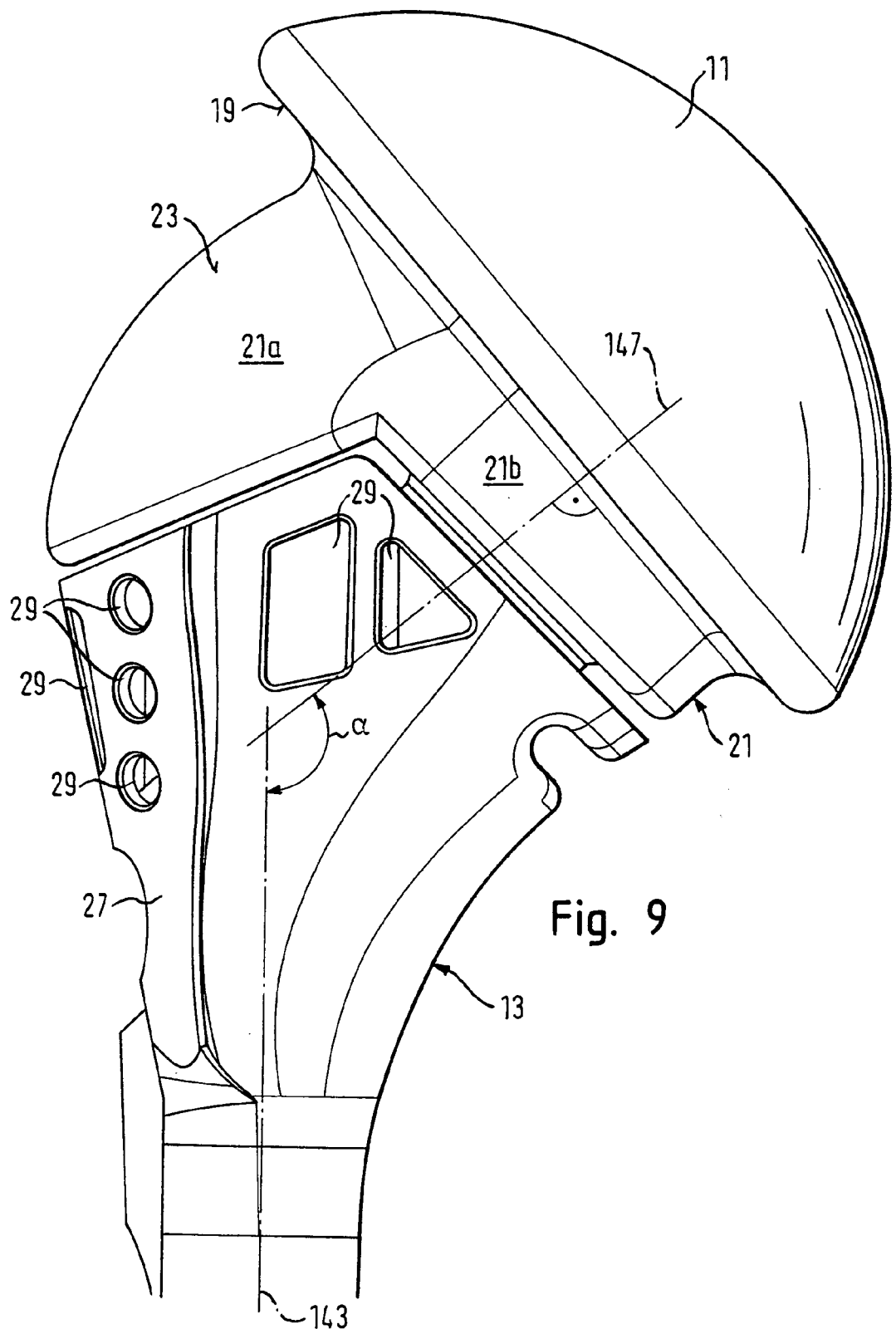
Figure 10:
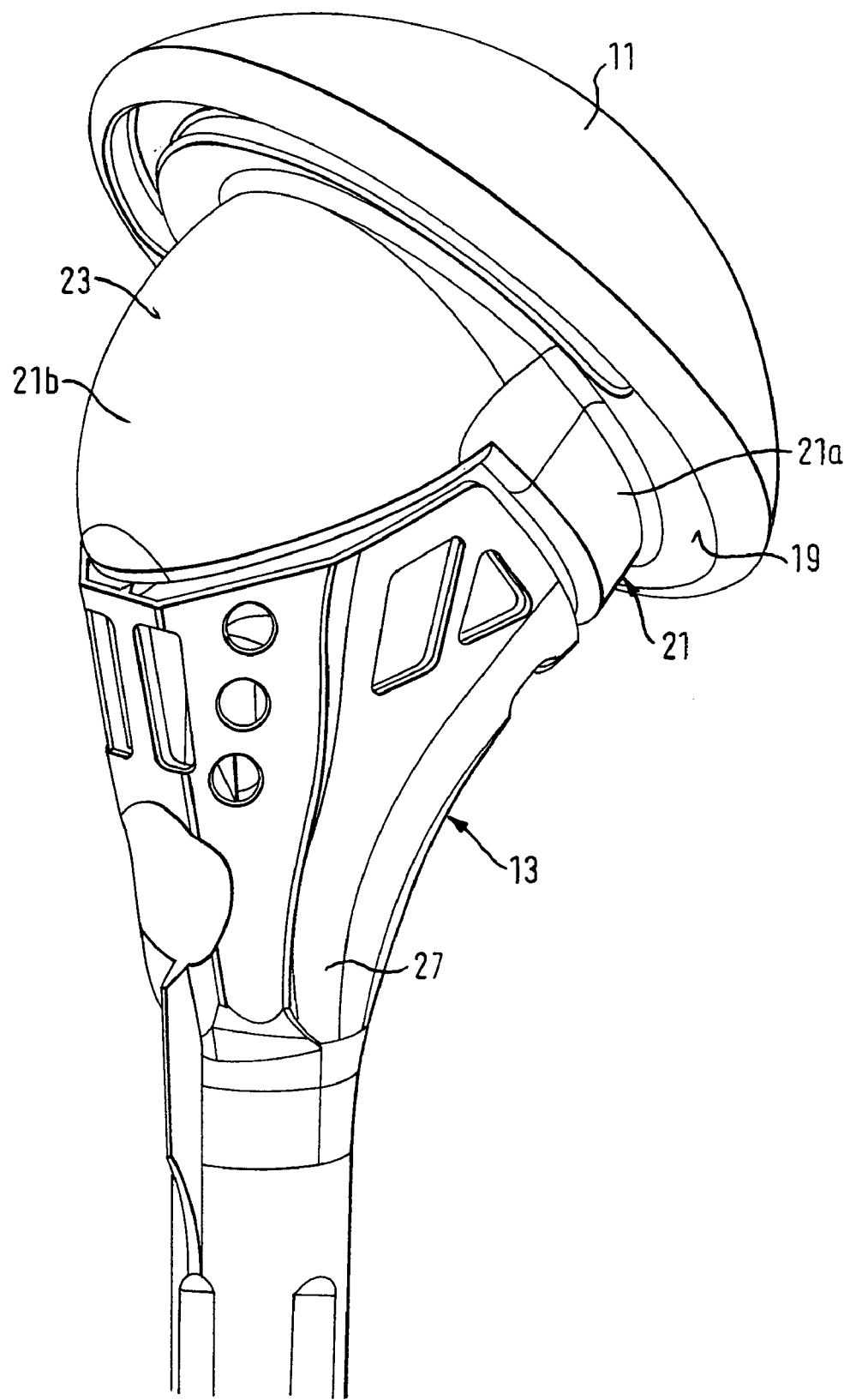
Figure 11:
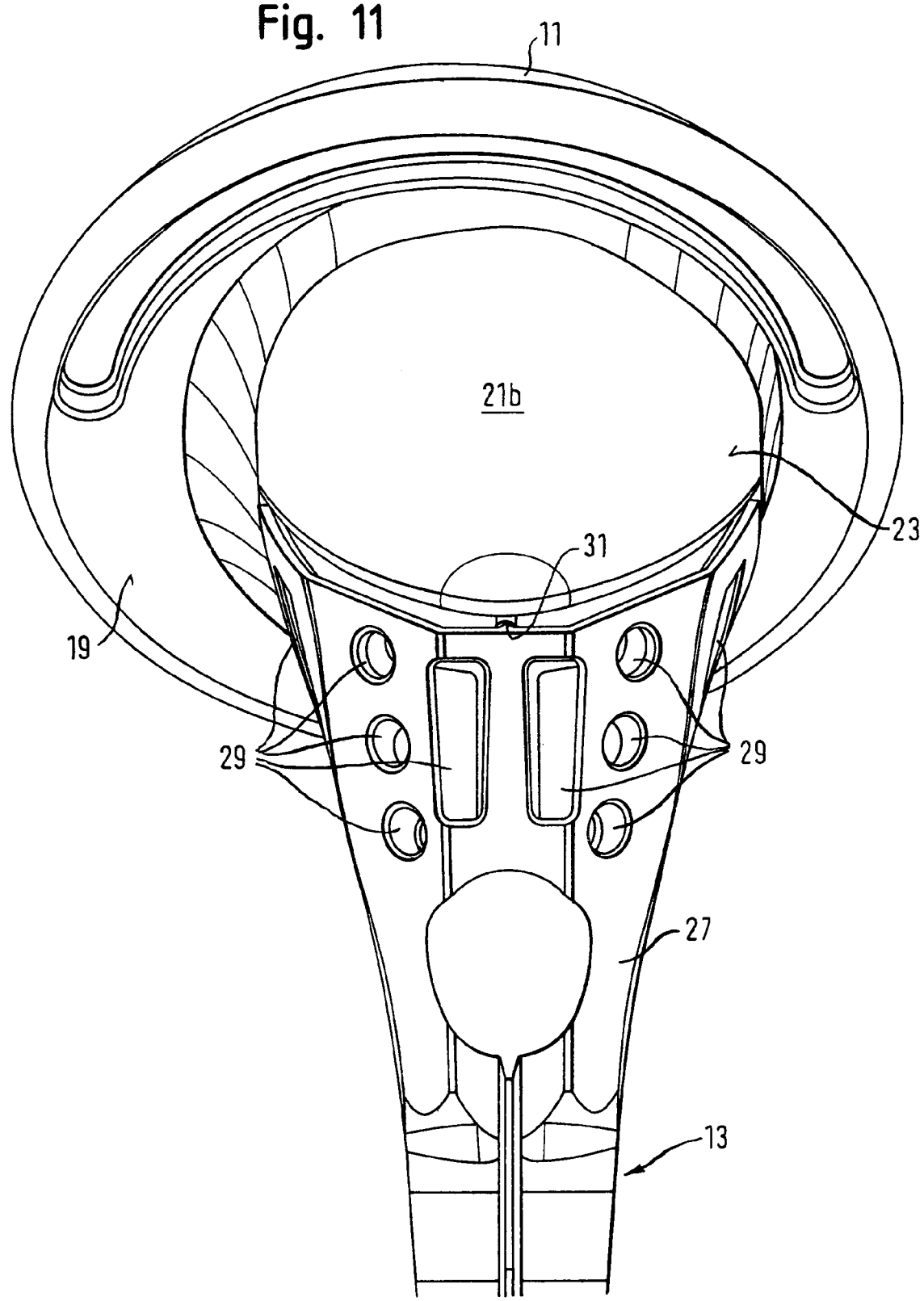
Figure 12:
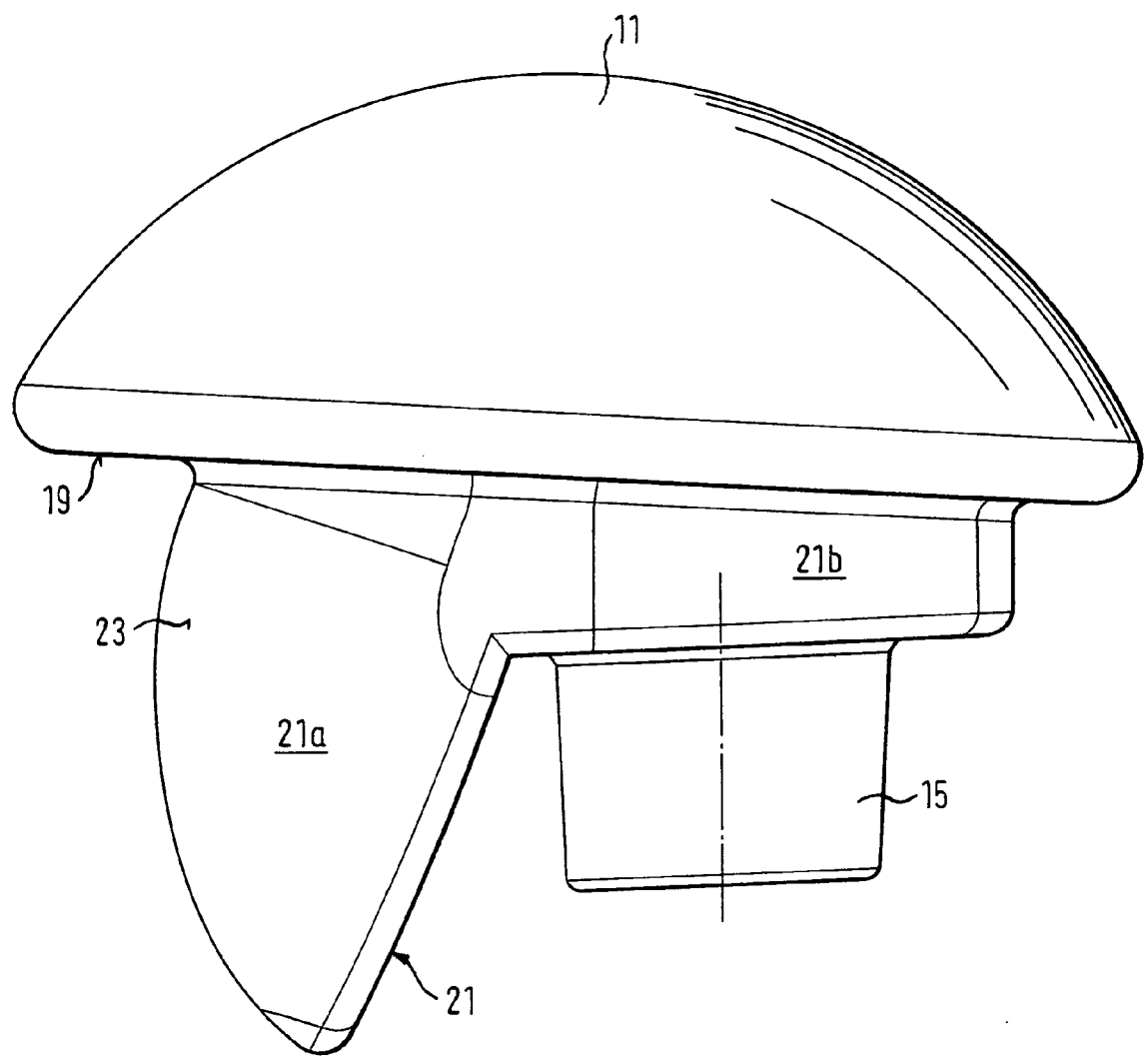
Figure 13:
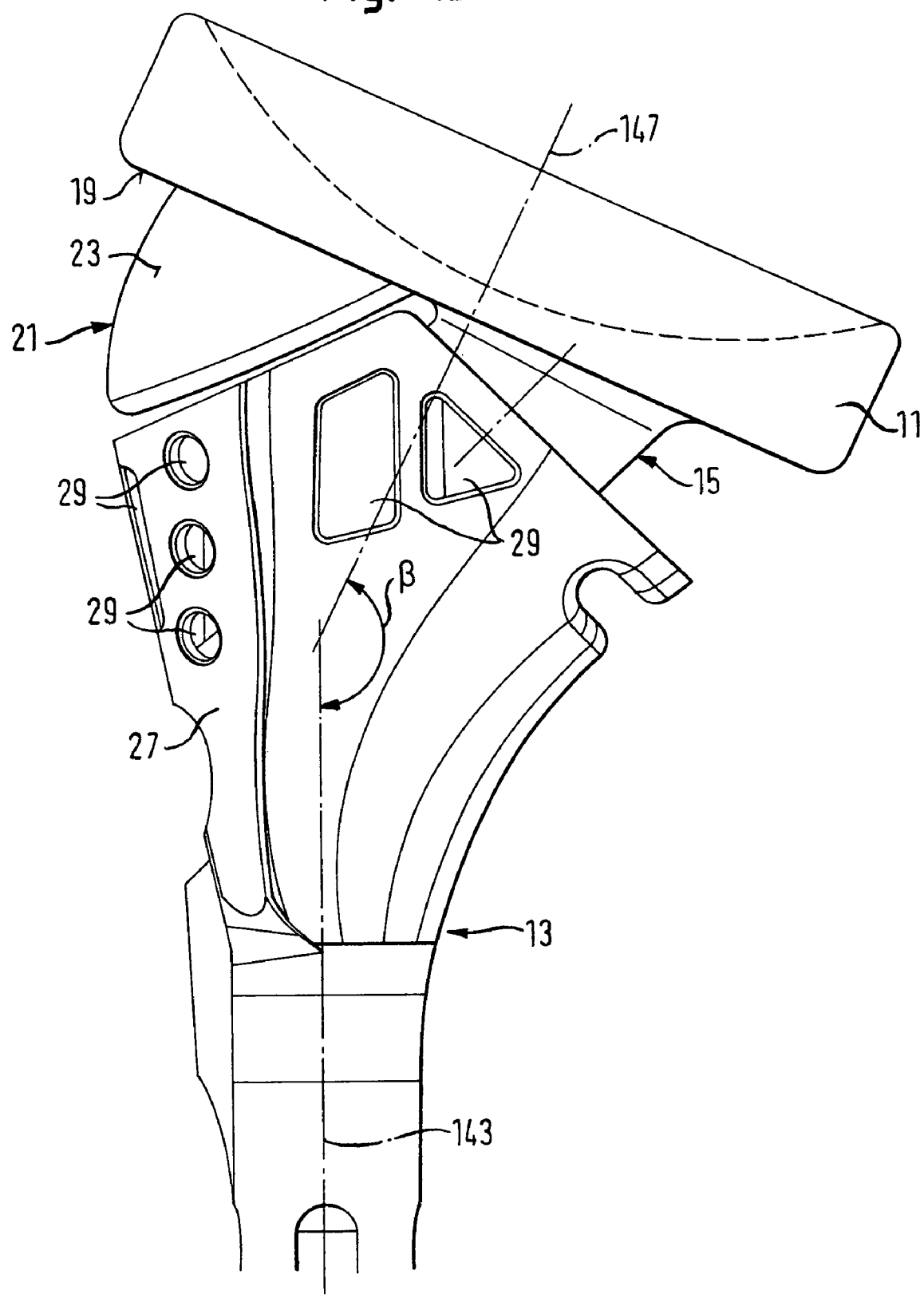
Figure 14:
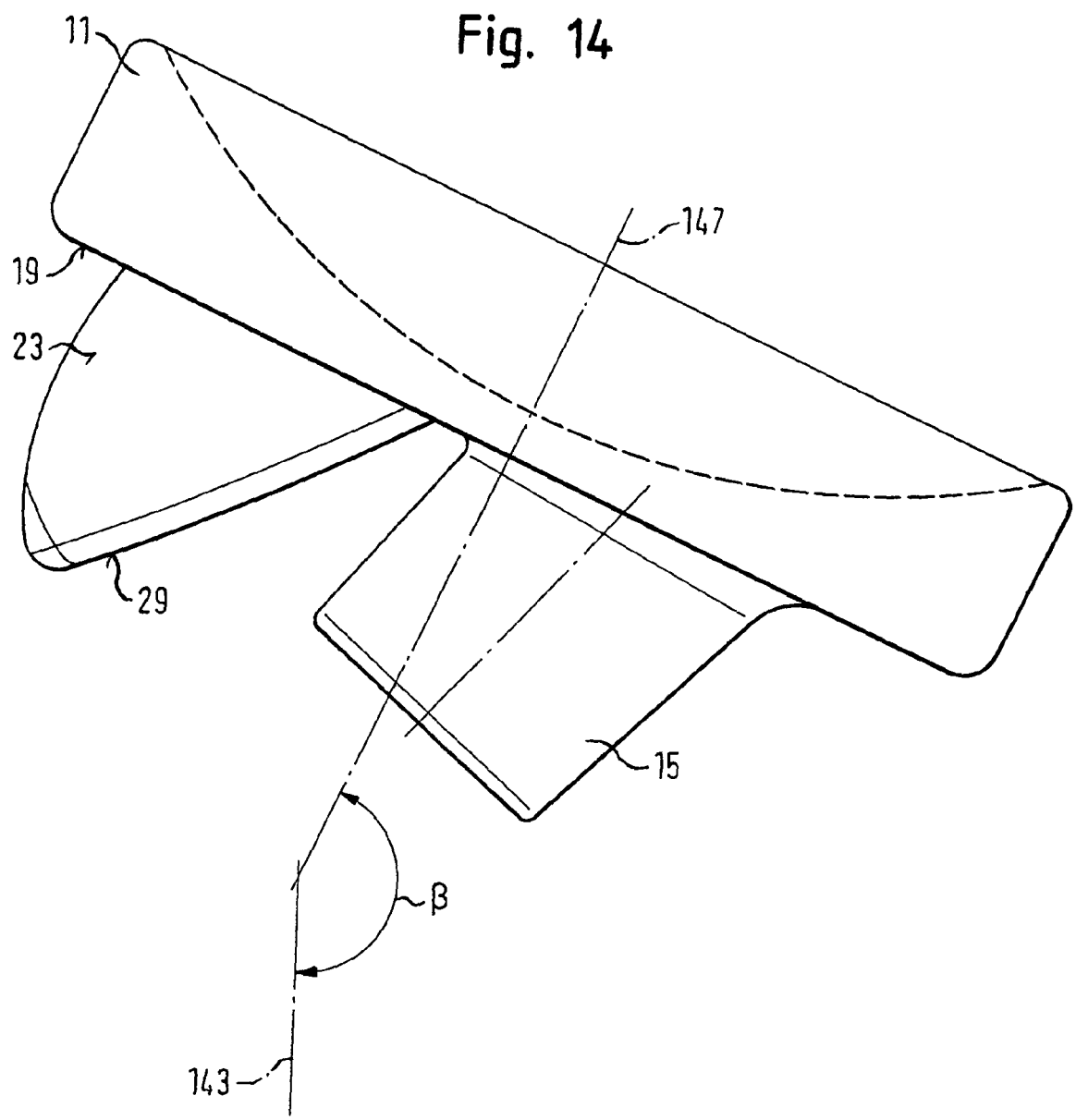
Figure 15:
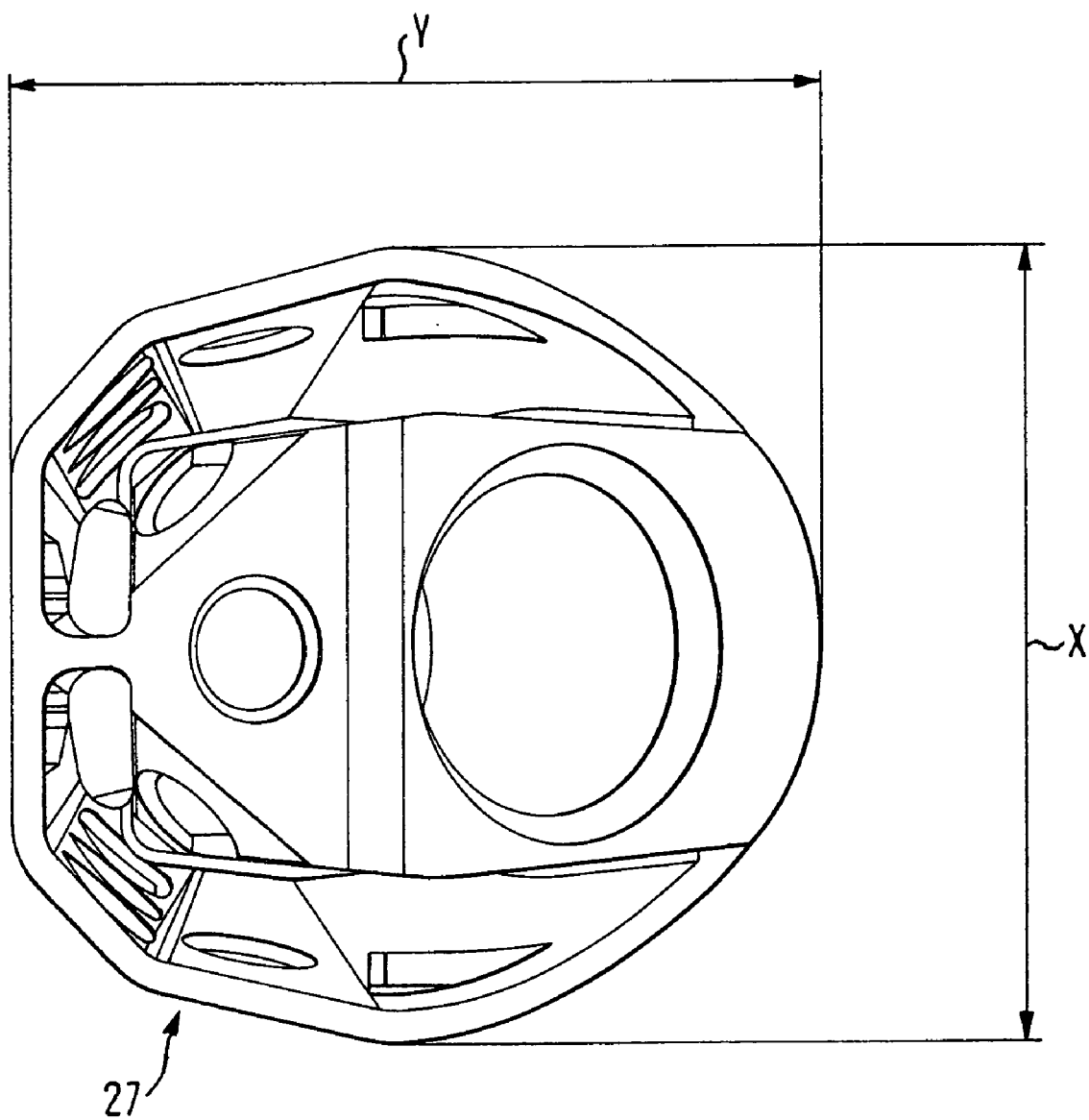
Figure 16B:
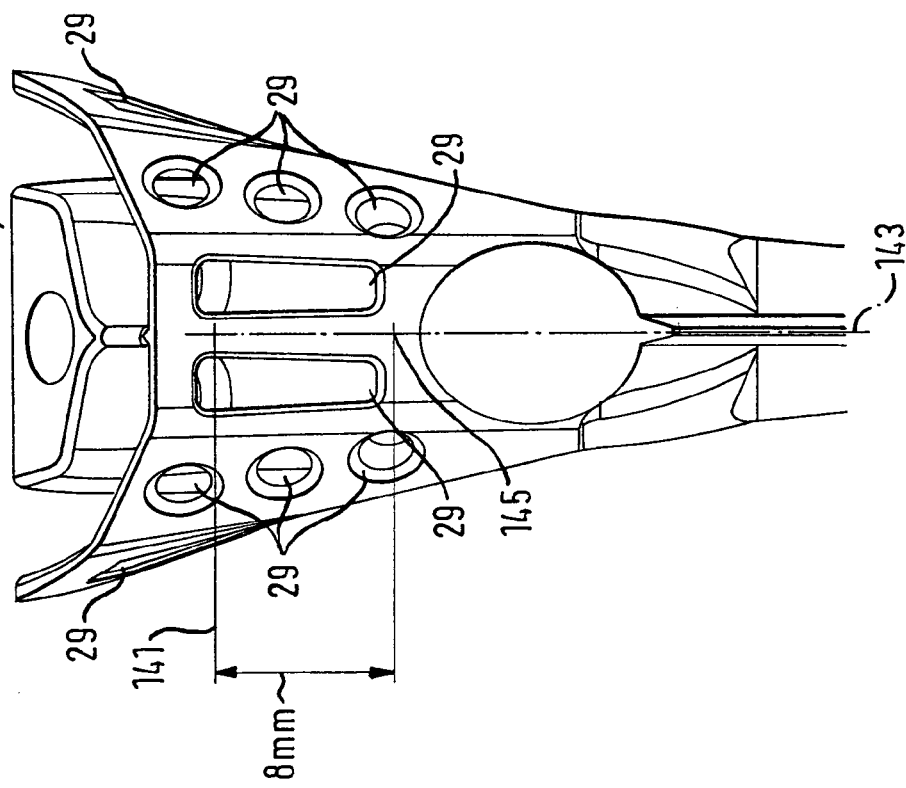
Figure 16A:
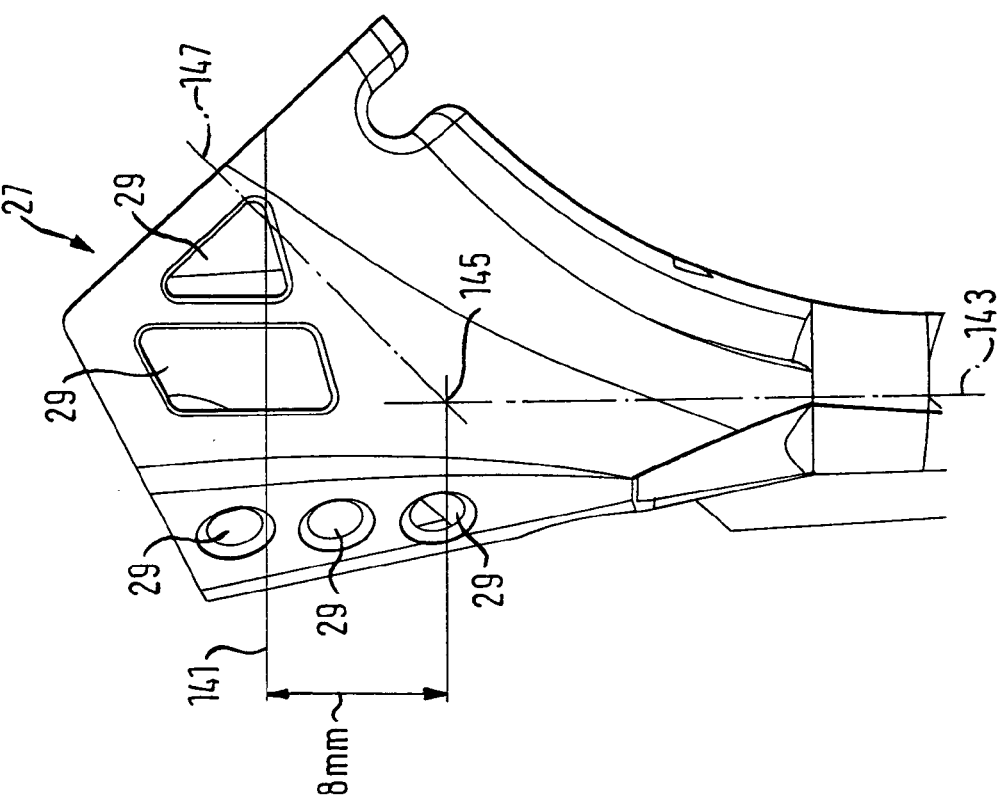

FIG. 4 schematically, a section in accordance with FIG. 3 at which a rotationally fixed wedging is shown between the conical body and the counter shape;

FIG. 5 schematically, a section through a conical body having an originally rectangular cross-section in accordance with the prior art, at which conical part surfaces which are elliptical in section have been subsequently made to match a counter shape in accordance with FIG. 4;

FIG. 6 schematically, a conical body in accordance with the prior art in which an aperture has been worked into the central region of the conical surface;

FIG. 7 schematically, a shaft of the prior art implanted into a humerus with a counter shape for a conical body;

FIG. 8 schematically, a conical body which matches the shaft of FIG. 7 and which together with a bearing body formed as a spherical shell forms an artificial shoulder joint to a spherical head in accordance with the prior art which is fastened to the shoulder bone via a platform;

FIG. 9 a part of a shoulder joint prosthesis in accordance with the invention with a bearing body formed as a bearing head in the state connected to a shaft;

FIG. 10 another view of the shoulder joint prosthesis in accordance with the invention of FIG. 9;

FIG. 11 a further view of the shoulder joint prosthesis in accordance with the invention of FIG. 9;

FIG. 12 the bearing body of the shoulder joint prosthesis in accordance with the invention of FIG. 9 provided with a support member and a clamping cone;

FIG. 13 a part of another embodiment of a shoulder joint prosthesis in accordance with the invention with a bearing body formed as a bearing shell;

FIG. 14 the bearing body of the shoulder joint prosthesis in accordance with the invention of FIG. 13 provided with a support member and a clamping cone;

FIG. 15 a view from above of a support element of a shoulder joint prosthesis in accordance with an embodiment of the invention to explain an outer diameter ratio; and FIGS. 16a and 16b different views of the support element of FIG. 15.

FIGS. 1 to 8 show a shoulder joint prosthesis in accordance with the prior art whose features, which, with one exception which will be looked at below, are also or can also be the subject of the shoulder joint prosthesis in accordance with the invention. To this extent, FIGS. 1 to 8 and the associated description are to be considered as disclosed as belonging to the invention. The exception mentioned lies in the fact that the bearing bodies 101, 112 of the prior art do not have a support member such as will be explained below in connection with FIGS. 9 to 14.

FIGS. 1 and 2 show a first embodiment of a known shoulder joint prosthesis. A shaft 105 is implanted in a humerus 103, with the shaft 105 being directly anchored in a prepared bone bed. The shaft 105 can, however, equally well be a shaft 105 anchored in the humerus 103 with bone cement.

A bore 116, which ends in a counter shape 115 for a conical body 107, is provided for the actual shoulder joint in the direction of a longitudinal axis 109. The actual joint is formed by a bearing head 101 rigidly connected to the conical body 107 and by a bearing shell 102 which is in turn rigidly connected to a platform 106 anchored in the shoulder bone 104.

Spigots 114, which extend parallel to one another, are attached to the platform 106 for the anchoring of the platform 106 and are anchored, for example, with bone cement or by a press fit in prepared bores of the shoulder bone 104.

The conical body 107 here forms a coupling serving as a clamping section for the connection of the bearing body formed as a bearing head 101 in the example of FIGS. 1 and 2 to the shaft 105 which for this purpose has the counter shape 115 serving as a coupling mount or receiver for the clamping cone 107.

The conical body 107—and accordingly the counter shape 115—each have a cross-section 110 with a periphery 108 which is elliptical in form in accordance with FIG. 3.

In FIG. 4, the desired relationships in an approximately elliptical cross-section are shown. Four contact points P, which expand to contact areas on intense pressing, are provided by slight shape deviations between the conical body 107 and the counter shape 115.

A radial spacing 139 of a contact point P is selected such that a line of application of a normal force N leads past the longitudinal axis 109 at a relatively large distance at a central point P in order to transmit portions of a torque M as changes of normal forces.

A torque M additionally acting at the conical body 107 is compensated in this manner by a reduction in the bias or by an increase in the bias N by a fraction ΔN. The biased local shape match is therefore decisive.

The same situation is shown in more extreme form in FIG. 5. The conical body 105 is only in contact with the elliptical base shape 115 in the region of the contact points expanded to contact areas. The remaining areas are recessed.

A further possibility for a modification of the conical body 107 is shown in FIG. 6. To be able to transfer bending moments which are as large as possible in the longitudinal axis 109, the tensioning takes place in two cross-sections which lie apart by a minimum spacing 137. This means that the cone 107 has an interruption 138 of this minimum spacing 137 in the central region.

In the second embodiment of a known shoulder joint prosthesis in accordance with FIGS. 7 and 8, the functions of the spherical shell and of the bearing shell have been swapped over to allow the upper arm to rotate about a center of motion. The bearing body 112, which can be connected to the shaft 105, is here provided in the form of a bearing shell formed as a spherical shell.

The shaft 105 implanted in the shaft 103 is provided with a bore 116 as well as with a counter shape 115 for a conical body 107. However, the conical body is broadened to receive the spherical shell 112 which in turn partly surrounds a spherical head 111. The spherical head 111 is fastened by a snap or screw connection (not shown) to a platform 106 which is anchored in the shoulder bone 104 via spigots 114. The anchoring of the platform 106 can equally well take place in the shoulder bone 104 via bone screws and projecting ribs.

Strength calculations and practical trials have shown that, with an arrangement having an elliptical cross-section of the conical body 107 and of its counter shape 115, an optimum utilization of the material takes place when the ellipse is aligned in its plane such that its major axis appears as a perpendicular in a protection toward lateral. Such an arrangement allows a maximum strength to be achieved for the conical clamping connection between the conical body 107 and its counter shape 115 with a width of the shaft 105 restricted from anterior to posterior. This applies both to arrangements having a full conical body 107 and to a conical body having a bore, as long as the shaft 105 has a lower thickness from posterior to anterior transversely to the longitudinal axis 109 than in other directions.

FIGS. 9 to 11 show a part of a shoulder joint prosthesis in accordance with the invention in which a bearing body 11 formed as a bearing head is connected to a shaft 13. FIG. 12 shows the bearing body 11 without the shaft 13. The bearing body 11 is connected to a clamping section 15 which is formed as a cone with an elliptical cross-section and which can be hammered into a correspondingly formed counter shape of the shaft 13 in order to establish a firm clamping seat of the cone 15 in the shaft 13 which can be released again.

The orientation of the bearing body 11 relative to the cone 15 can be selected as desired during the operation within certain limits in accordance with the respective circumstances. For this purpose, the cone 15 is provided with a coupling section (not shown) on which the bearing body 11 is supported. This coupling section is moreover formed such that the bearing body 11 can be fixed in a relative position with respect to the cone 15 selected during the operation.

This adjustable and fixable coupling between the cone 15 and the bearing body 11 is not a subject of the present invention so that it is not looked at in any more detail.

In accordance with the invention, the bearing body 11 is provided with a support member 21. The support member 21 can be made in one piece with the bearing body 11 or be provided as a separate component connectable to the bearing body 11. The connection between the support member 21 and the bearing body 11 can be made so firmly that the bearing body 11 and the support member 21 form a fixed, rigid configuration. Alternatively, it is basically also possible to attach the support member 21 to the bearing body 11 in an adjustable manner to be able to set a configuration suitable for the respective application.

In the embodiment shown, the support member 21 includes a shell-like section 21b and a collar-like section 21a whose height, i.e. its extent perpendicular to the lower side 19 of the bearing body 11, decreases in the direction facing away from the collar-like section 21a.

The support member 21 serves to close the intermediate space which is present between the lower side 19 of the bearing body 11 and the shaft 13 when the bearing body 11 is connected to the shaft 13 and to make available a support surface 23 with its outer side at which bone fragments can be supported, whereby their growing together is promoted.

In the embodiment shown, the support surface 23 of the support member 21 adjoins the jacket surface of the shaft 13 which is here formed in the region of the transition from the shaft 13 into the support member 21 by a basket-like support element 27 mounted on the shaft 13 from the side which will be looked at in more detail in the following.

The provision of such a support basket 27 is, however, not mandatory. The support member 21 in accordance with the invention can generally also be used without a support basket 27 provided at the shaft 13.

Apart from apertures 29 formed in the support basket 27, the support surface 23 of the support member 21 and the jacket surface of the shaft 13 formed in the transition region from the outer side of the support basket 27, which is of interest here, together form a closed area adjoining the lower side 19 of the bearing body 11. The convex support surface 23 tangentially adjoins the jacket surface of the shaft 13 or the outer side of the support basket 27.

As FIG. 11 in particular shows, a recess 31 is present between the support basket 27 of the shaft 13 and the shell-like section 21b of the support member 21, when the bearing body 11 is connected to the shaft 13, and a tool can be positioned thereat to release the bearing body 11 from the shaft 13.

In the embodiment of the shoulder joint prosthesis in accordance with the invention shown in FIGS. 13 and 14, the bearing body 11 is formed as a spherical shell. The support member 21 here includes only one shell-like section whose outer side forms the support surface 23. An additional collar-like section is not provided in this example, with the support member 21, however, generally also being able to have an additional support section, e.g. in collar form, in the case of shoulder joint prostheses with a bearing body 11 formed as a spherical shell. Apart from this, what was said in connection with the Figures explained above also applies to this embodiment.

The angles $\alpha$, $\beta$ drawn in FIGS. 9, 13 and 14 between the shaft axis 143 and the head or shell axis 147 are each selected in dependence on the respective anatomic circumstances. In the embodiments shown, $\alpha=130°$ and $\beta=155°$ applies.

FIG. 15 shows the basket-shaped or quiver-shaped support element 27 in a view from above along the shaft axis 143 (cf. e.g. FIGS. 9 and 13), i.e. the shaft axis 143 extends perpendicular to the drawing plane in FIG. 15.

With respect to the orientation of the support element 27 in the implanted state with the shaft axis 143 extending perpendicular to the transverse plane, the maximum outer diameter in the sagittal direction X and the maximum outer diameter in the transverse direction Y have been selected such that the ratio X/Y lies in the range from 0.85 to 0.95 for all sizes of the support element 27 provided in an implant set.

It has furthermore been found to be advantageous to provide the apertures 29 in the support element 27 such that the condition explained in the following with reference to FIGS. 16a and 16b is satisfied.

The apertures 29 have been made and positioned such that the proportion of the sections of the outer surface of the support element 27 interrupted due to the apertures 29 lies in the region from 35% to 45% along a peripheral line 141 of the support element 27 which lies in a plane in the implanted state which extends perpendicular to the shaft axis 143 and, in a proximal direction, at a spacing of 8 mm from the point of intersection 145 between the shaft axis 143 and the head axis or shell axis 147.

Trials have shown that an optimum compromise hereby takes place between a support of fragments of the bone fracture and their growing together with bone chips introduced through the apertures 29.

REFERENCE NUMERAL LIST 11 bearing body
13 shaft
15 coupling, clamping section, cone
19 lower side of the bearing body
21 support member
21a collar-shaped section of the support member
21b shell-shaped section of the support member
23 support surface 27 support element, support basket, support quiver
29 aperture
31 recess
101 bearing head
102 bearing shell
103 humerus
104 shoulder bone
105 shaft
106 platform
107 conical body
108 periphery
109 longitudinal axis
110 cross-section
111 spherical head
112 spherical shell
114 spigot
115 counter form
116 bore
136 spacing
137 minimum spacing
138 interruption
139 radial spacing
141 peripheral line
143 shaft axis
145 point of intersection
147 head axis, shell axis

What is claimed is:

1. A shoulder joint prosthesis comprising two cooperating bearing bodies (11), a shaft (13) and a coupling (15) for the connection of the shaft (13) to one of the bearing bodies (11), wherein a support member (21) adjoins a lower side (19) of the bearing body (11) connectable to the shaft (13), an outer support surface (23) of said support member (21) at least partly filling a gap present between the bearing body (11) and the shaft (13) in the state connected to the shaft (13) such that the growing together of bone fragments is promoted;
wherein the shaft (13) is provided with a support element (27), having a basket-like or quiver-like shape, which is mounted laterally at the shaft (13) and whose outer side forms a jacket surface of the shaft (13) merging into the support surface (23) of the support member (21) in the region of the transition from the shaft (13) into the support member (21); and
wherein the support element (27) is provided with apertures (29).

2. A shoulder joint prosthesis in accordance with claim 1, wherein the coupling for the connection of the shaft (13) includes a clamping section (15) with which a firm clamping seat of the coupling (15) in the shaft (13) can be established by introducing into a coupling mount of the shaft (13), in particular a clamping seat which can be released again.

3. A shoulder joint prosthesis in accordance with claim 2, wherein the clamping section (15) tapers like a cone and can be introduced into a correspondingly shaped counter shape of the shaft (13) as a coupling mount.

4. A shoulder joint prosthesis in accordance with claim 2, wherein the clamping section (15) forms a shape matched connection with the counter shape which is rotationally fixed with respect to a longitudinal axis and is wedged by its conical shape in the state connected to the shaft (13).

5. A shoulder joint prosthesis in accordance with claim 2, wherein the clamping section (15) has a cross-section deviating from a circular shape.

6. A shoulder joint prosthesis in accordance with claim 2, wherein the clamping section (15) has an elliptical cross-section.

7. A shoulder joint prosthesis in accordance with claim 6, wherein the elliptical cross-section of the clamping section (15) and of the counter shape of the shaft (13) is aligned in its plane such that the major axis of the ellipse appears as a perpendicular in a projection toward lateral.

8. A shoulder joint prosthesis in accordance with claim 6, wherein the shaft (13) has, in the plane of the elliptical cross section, the outline of a rectangle provided with rounded corners whose long sides extend parallel to the major axis of the ellipse.

9. A shoulder joint prosthesis in accordance with claim 1, wherein the support member (21) is replaceably connected to the bearing body (11).

10. A shoulder joint prosthesis in accordance with claim 1, wherein the support element (27) is fixedly connected to the shaft (13) and is in particular welded to the shaft.

11. A shoulder joint prosthesis in accordance with claim 1, wherein the support element (27) is made in one piece with the shaft (13).

12. A shoulder joint prosthesis in accordance with claim 1, wherein the proportion of the sections of the outer surface of the support element (27) interrupted due to the apertures (29) lies in the range from 35% to 45% along a peripheral line (141) of the support element (27) which lies in the implanted state in a plane extending perpendicular to the shaft axis (143) and, in the proximal direction, at a spacing of 8 mm from the point of intersection (145) between the shaft axis (143) and the head axis or shell axis (147).

13. A shoulder joint prosthesis comprising two cooperating bearing bodies (11), a shaft (13) and a coupling (15) for the connection of the shaft (13) to one of the bearing bodies (11), wherein a support member (21) adjoins a lower side (19) of the bearing body (11) connectable to the shaft (13), an outer support surface (23) of said support member (21) at least partly filling a gap present between the bearing body (11) and the shaft (13) in the state connected to the shaft (13) such that the growing together of bone fragments is promoted; and
wherein, when the bearing body (11) is connected to the shaft (13), at least one recess (31) is present between the shaft (13) and the support member (21) at which a tool can be positioned to release the bearing body (11) from the shaft (13).

14. A shoulder joint prosthesis comprising two cooperating bearing bodies (11), a shaft (13) and a coupling (15) for the connection of the shaft (13) to one of the bearing bodies (11), wherein a support member (21) adjoins a lower side (19) of the bearing body (11) connectable to the shaft (13), an outer support surface (23) of said support member (21) at least partly filling a gap present between the bearing body (11) and the shaft (13) in the state connected to the shaft (13) such that the growing together of bone fragments is promoted;
wherein the shaft (13) is provided with a support element (27), having a basket-like or quiver-like shape, which is mounted laterally at the shaft (13) and whose outer side forms a jacket surface of the shaft (13) merging into the support surface (23) of the support member (21) in the region of the transition from the shaft (13) into the support member (21); and
wherein, with respect to the orientation of the support element (27) in the implanted state with the shaft axis (143) extending perpendicular to the transverse plane, the ratio X/Y of the maximum outer diameter of the support element (27) in the sagittal direction X and the maximum outer diameter of the support element (27) in the transverse direction Y lies in the range from 0.85 to 0.95.

* * * * *